United States Patent [19]

Granek et al.

[11] Patent Number: 4,729,377

[45] Date of Patent: * Mar. 8, 1988

[54] GARMENT APPARATUS FOR DELIVERING OR RECEIVING ELECTRIC IMPULSES

[75] Inventors: Herman Granek, Miami Beach; Murry Granek; John Church, both of Miami, all of Fla.

[73] Assignee: Bio-Stimu Trend Corporation, Opa Locka, Fla.

[ * ] Notice: The portion of the term of this patent subsequent to Apr. 8, 2003 has been disclaimed.

[21] Appl. No.: 611,731

[22] Filed: May 22, 1984

Related U.S. Application Data

[63] Continuation-in-part of Ser. No. 499,866, Jun. 1, 1983, Pat. No. 4,580,572, and a continuation-in-part of Ser. No. 517,810, Jul. 27, 1983, Pat. No. 4,583,547.

[51] Int. Cl.⁴ .......................... A61B 5/04; A61N 1/04
[52] U.S. Cl. ..................... 128/639; 128/644; 128/799; 128/802; 128/803
[58] Field of Search ................. 128/639–641, 128/643, 644, 783, 791–793, 798, 799, 802, 803, 379, 384

[56] References Cited

U.S. PATENT DOCUMENTS

| | | | |
|---|---|---|---|
| 2,555,037 | 5/1951 | Jensen | 128/639 |
| 3,387,608 | 6/1968 | Figar | 128/640 |
| 3,409,007 | 11/1968 | Fuller | 128/644 |
| 3,474,775 | 10/1969 | Johnson | 128/639 |
| 3,610,229 | 10/1971 | Zenkich | 128/641 |
| 3,774,592 | 11/1973 | Lahr | 128/640 |
| 4,166,457 | 9/1979 | Jacobsen et al. | 128/639 |
| 4,239,046 | 12/1980 | Ong | 128/640 |
| 4,323,076 | 4/1982 | Sams | 128/644 |
| 4,381,012 | 4/1983 | Russek | 128/644 |
| 4,580,572 | 4/1986 | Granek et al. | 128/639 |

*Primary Examiner*—Lee S. Cohen
*Attorney, Agent, or Firm*—Eric P. Schellin

[57] ABSTRACT

A garment containing multiple conductive paths made of conductive cloth is used to connect an internal or external electrical apparatus to various points on the skin of the wearer. The garment can be designed for electrical monitoring of sites or electrical stimulation. Designated sites on the garment can be activated by soaking the site with conducting fluid.

17 Claims, 17 Drawing Figures

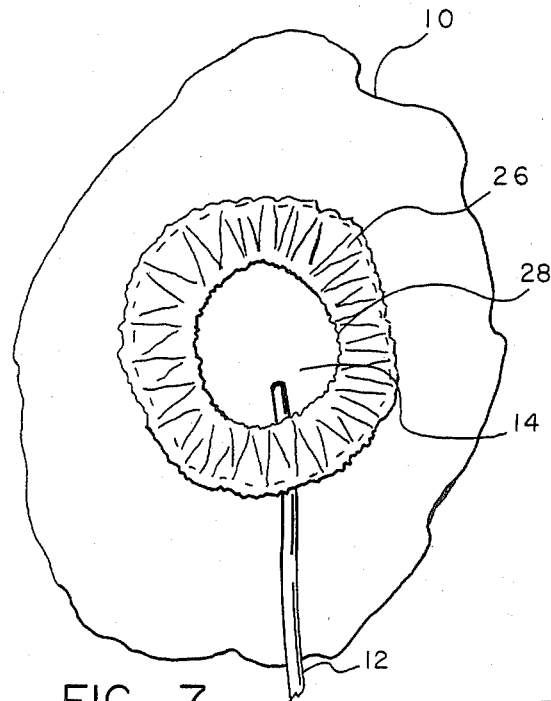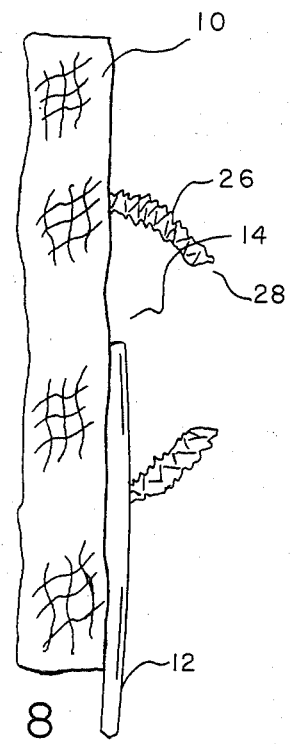# FIG. 7
FIG. 8
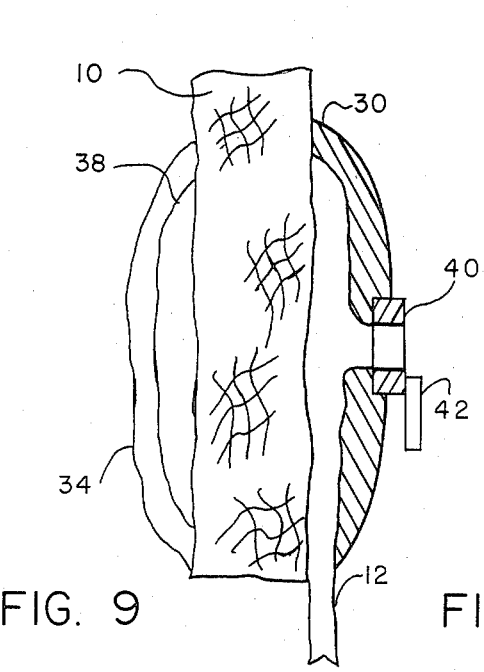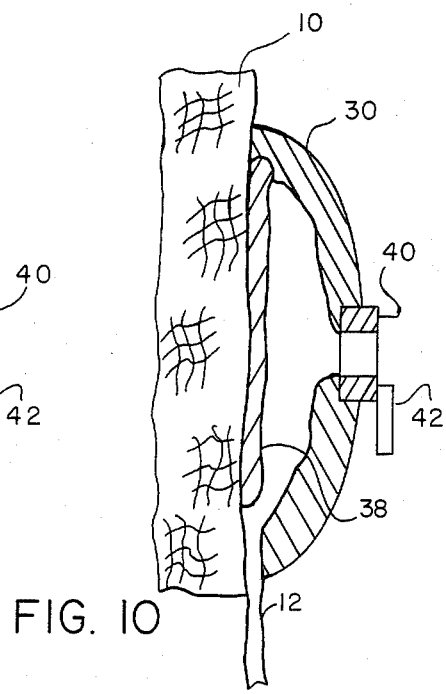
FIG. 9
FIG. 10

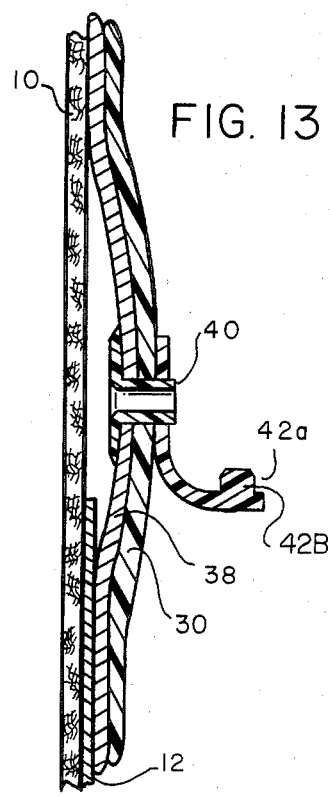
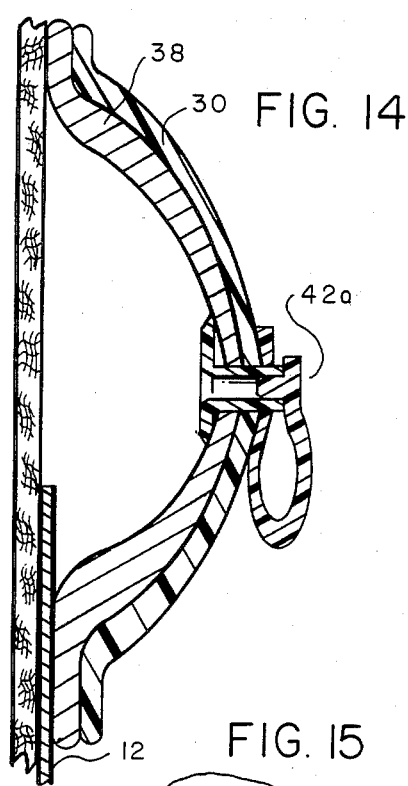
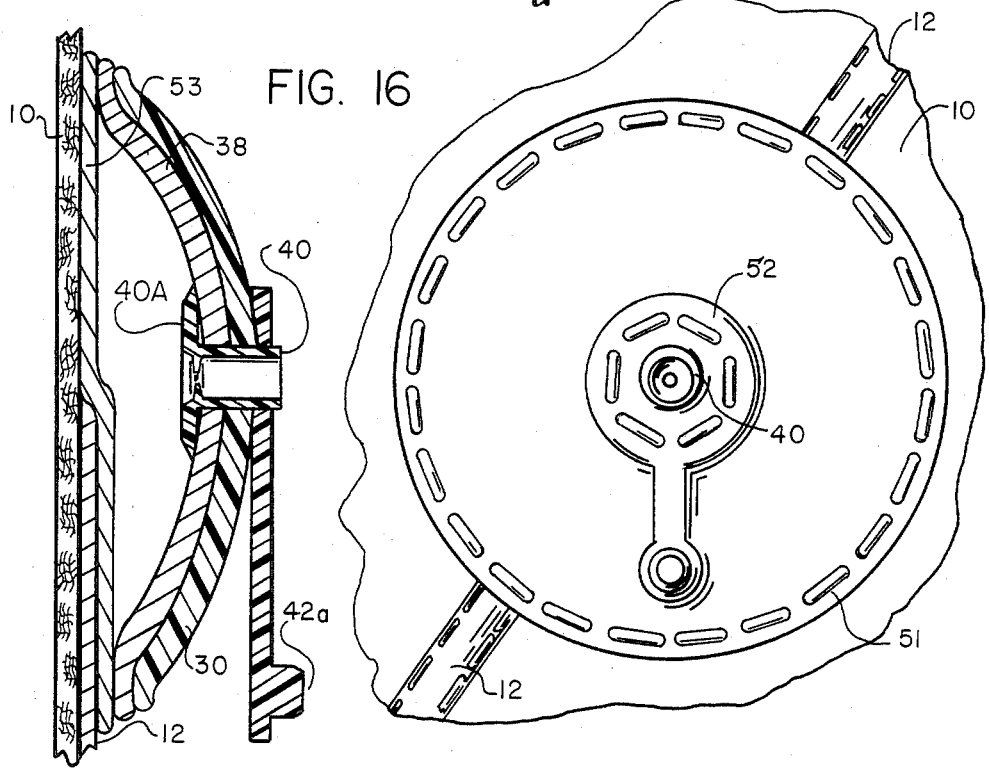

ND RECEIVING ELECTRIC IMPULSES

GARMENT APPARATUS FOR DELIVERING OR RECEIVING ELECTRIC IMPULSES

RELATED APPLICATIONS

This is a continuation-in-part of application Ser. No. 499,866 filed June 1, 1983, now U.S. Pat. No. 4,580,572, and is a continuation-in-part of application Ser. No. 517,810 filed July 27, 1983, now U.S. Pat. No. 4,583,547.

FIELD OF THE INVENTION

This invention is a garment containing conductive paths to different parts of the body having points of electrical contact with the skin selectable by applying an electrically conductive liquid through these preselected points in the garment.

BACKGROUND OF THE INVENTION

Various medical procedures require receiving electrical signals from various parts of the body or applying electrical signals to other points of the body. Among these procedures are T.E.N.S. (Transcutaneous Electrical Nerve Simulation), E.M.S. (Electrical Muscle Stimulation), F.E. S. (Functional Electrical Stimulation), EMG (Electromyograph), EEG (Electroencephalogram), EKG (Electrocardiogram), computer generated signal transmission for the purpose of motor stimulated movement in quadraplegic or paraplegic patients, transmission of signals to specific sites for the purpose of transcutaneous bone growth stimulation, and eductional systems to allow immediate and accurate identification of known anatomical points of importance in sending or monitoring biomedical signals. Current products for attachment to the body require individual wires and electrodes which hinder body movement and during body movement electrodes are often accidently disconnected. Many electrodes do not allow the skin to breathe; chemical properties sometimes irritate the skin requiring special skin care during long periods of monitoring or stimulation. Most electrodes require hair removal for proper attachment, and many points on the body are not suitable to standard electrode placement because of their peculiar anatomical configuration, movement or shape. Prior art devices for incorporating electrodes into garments have been generally limited to boots as in U.S. Pat. No. 3,941,137 to Vredenbregt et al, belts as in U.S. Pat. No. 502,776 to Se Cheverall and to masks as in U.S. Pat. No. 3,279,468 to LeVine. These devices are limited to certain areas of the body and cannot be generalized to fit most of the human body, including the torso, the legs and the arms.

SUMMARY OF THE INVENTION

One aim of this invention is to provide a means of applying electrodes to any part of the body while allowing body movement and keeping such electrodes secure. Another aim is to provide a method of conveniently and inexpensively selecting electrodes for use on a standard garment having potential electrodes and conductors for every potentially useful point on the skin. A further aim is to provide means of holding conducting fluid in the garment at designated points without staining outer garments. A further aim is to provide a reservoir for conducting fluid to allow for extended interface.

These aims are satisfied by constructing a garment of ordinary non-conductive cloth. Such a garment might be, by way of illustration, like a body stocking, a long-sleeved sweater, a panty-hose, long gloves or a mark. A multiplicity of points on the body useful for a particular application are marked on the garment as designated points. These designated points are electrically connected by conductors to a connector plug for attaching to an external or internal electrical device. In garments for monitoring or stimulation each designated point has its own conductor. In other garments for stimulation each designated point might share one of a relatively small number of conductors. In the latter case the designated point might be activated by applying a conductive liquid to the selected point. The conductors can be a conductive medium knitted or woven into cloth, wires sewn onto the cloth or conducting cloth sewn onto the non-conducting base. Various enhancements can be added to each designated point. For example, tubes which penetrate the garment can be used to speed the conductive fluid to the skin. Electrodes on the inside surface can also be applied for specific purposes. Electrode and conductor on the inside surface can be insulated from the skin and create a different aesthetic appearance. Pockets of cloth on the inside or outside surface can facilitate application of fluid and protect outer garments.

These and further operational and constructional characteristics of the invention will be more evident from the detailed description given hereinafter with reference to the figures of the accompanying drawings which illustrate one preferred embodiment and alternatives by way of non-limiting examples.

BRIEF DESCRIPTION OF THE DRAWINGS

FIG. 7 shows a designated point with a pocket in plan view.

FIG. 8 shows the designated point of FIG. 7 in sectional view.

FIG. 9 shows an inside insulated electrode in sectional view.

FIG. 10 shows an outside insulated electrode in sectional view.

FIG. 13 is a cross-sectional view of still another embodiment of an electrode means in place.

FIG. 14 is the embodiment of FIG. 13 with electrolytic gel in place.

FIG. 15 is a top plan view of the embodiments of FIGS. 13 and 14.

FIG. 16 is a cross-sectional view of still another embodiment of an electrode means in place.

DESCRIPTION OF THE PREFERRED EMBODIMENT

Figure 1:
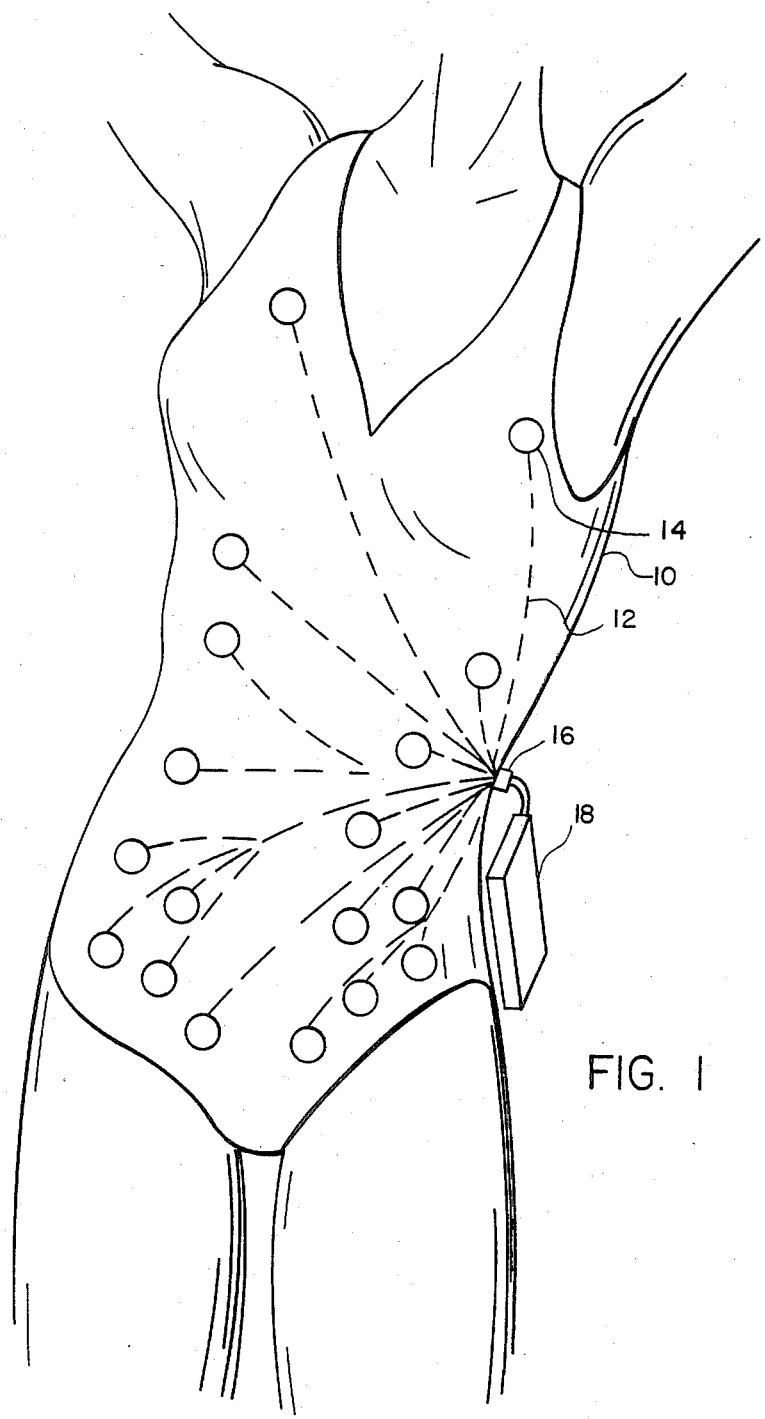
FIG. 1 shows the garment with multiple designated points each with individual conductors.

Referring now to the drawings wherein reference numerals are used to designate parts throughout the various figures thereof, there is shown in FIG. 1 a garment 10 in the form of a covering for the human torso, having embedded in the garment a multiplicity of insulated conductors 12 such as wires or conducting thread. One end of each conductor 12 is terminated at designated points 14 and the other end of each conductor is terminated in one or more connectors 16. The connector 16 is used to connect the garment 10 to the external device 18 for monitoring or supplying stimulating impulses. The garment might be constructed to cover the upper torso and the arms and might have integral gloves or a mask. The garment might be constructed to cover only the lower torso and the legs as in panty-hose. The garment might be one piece, covering the entire body or only as much as desired. The garment might be several pieces worn at the same time and connected externally to cooperating electrical units such as external device 18.

Figure 2:
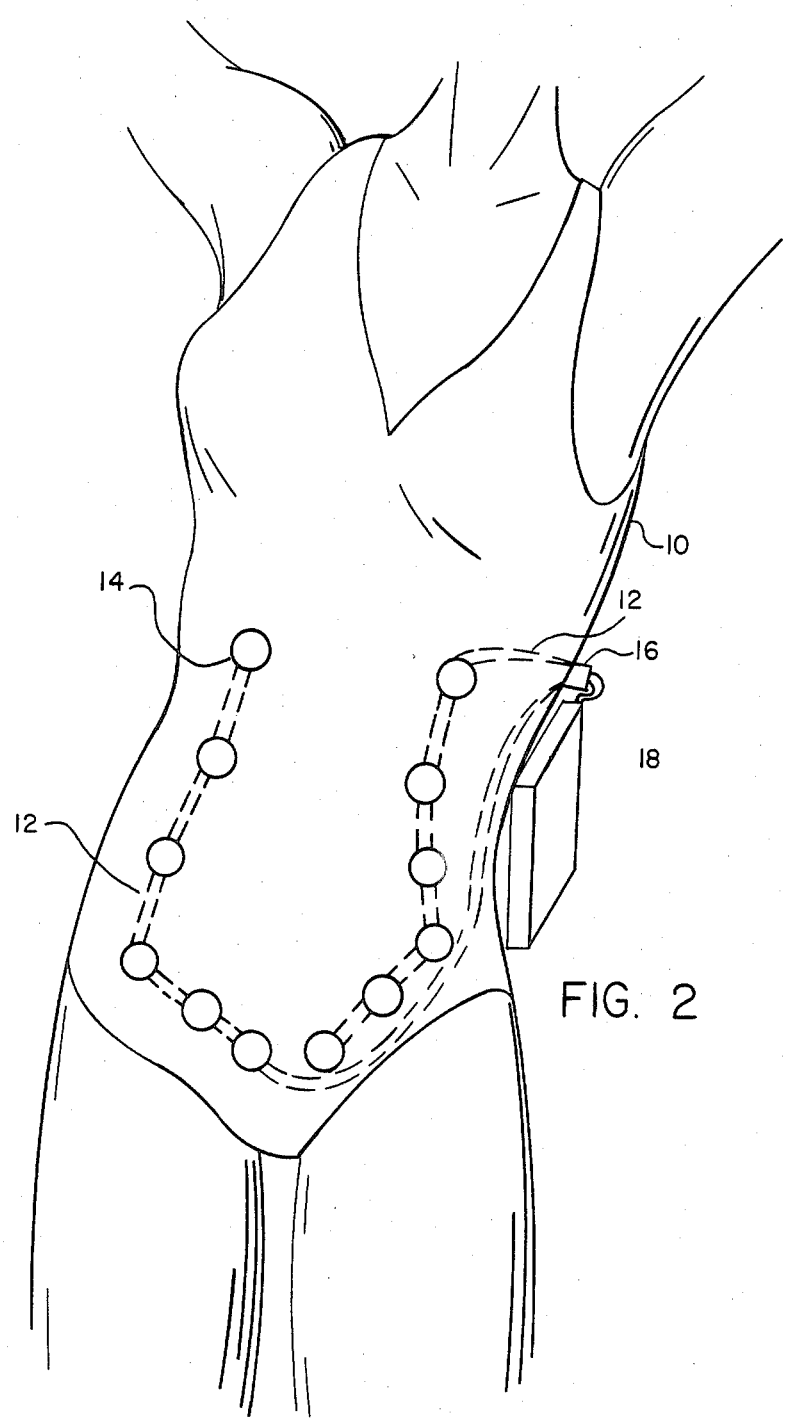
FIG. 2 shows the garment with multiple designated points connected to only two conductors.

Referring now to FIG. 2, the garment 10 is shown with the designated points 14 connected by multiple paths through conductors 12 on the outside of the garment 10 to the connector 16 and then to the external device 18.

The garment 10 will, in general, be made of nonconducting materials, in order to insulate different paths of conductors 12 from each other and patient's skin. Selected designated points may be made of donductive cloth for special purposes.

Such conductive cloth might be, for example, HI-MEG R Conductive Products, distributed by VELCRO USA, Inc. HI-MEG products are conductive in low voltage and amperage ranges. A resistance factor of 2 ohms per square inch is the maximum obtainable in any of the HI-MEG products provide a method of static charge effecting bleed-off rates up to 100% in a standard material run if the surface is conductive. By positioning additional thicknesses of HI-MEG material at several locations, on a non-conductive surface within one operation, static will be even further reduced. HI-MEG products maintain their effectiveness at static elimination at very low humidity levels (down to 0%) and will perform in a vacuum to reduce static on recording tapes. HI-MEG products can also be used to induce static electricity if desired. Cycling does not affect the conductivity unless the silver coating is excessive, causing a brittle coating which may fracture in flexing. Additional testing has been done to insure that HI-MEG products will continue to perform after normal exposure and maintenance. The results are summarized below: (1) there might be a slight amount of staining if the HI-MEG loop is rubbed against a light colored surface. (2) HI-MEG products can be commercially dry-cleaned or laundered, but many detergents or soaps might leave a film which will reduce its conductivity; therefore, good rinsing is a must. (3) Although HI-MEG products will tarnish due to their silver content, this tarnishing does not reduce their effectiveness. An exception to this rule is tarnish which is produced in a sulfur rich environment. (4) Conductivity is reduced by one-half to two-thirds after a 48 hour exposure to a salt spray.

Figure 3:
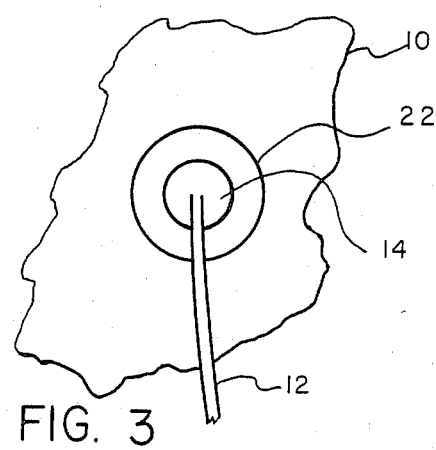
FIG. 3 shows a designated point with a tubular cylinder in plan view.
Figure 4:
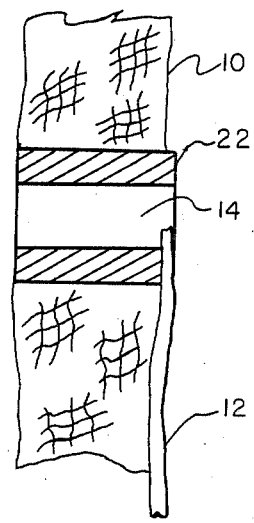
FIG. 4 shows the designated point of FIG. 3 in sectional view.

Referring now to FIGS. 3 and 4 of the accompanying drawings, in one embodiment the garment 10 might have tubular cylinders 22 inserted at the designated points 14. In general, the tubular cylinder 22 aids the insertion of conductive fluid into and under the garment; the tubular cylinder 22 might be, in general, a non-electrically-conductive material. In another embodiment, the tubular cylinder 22 might be made of electrically-conductive material and ends of the conductors 12 secured to the tubular cylinder 22.

Figure 5:
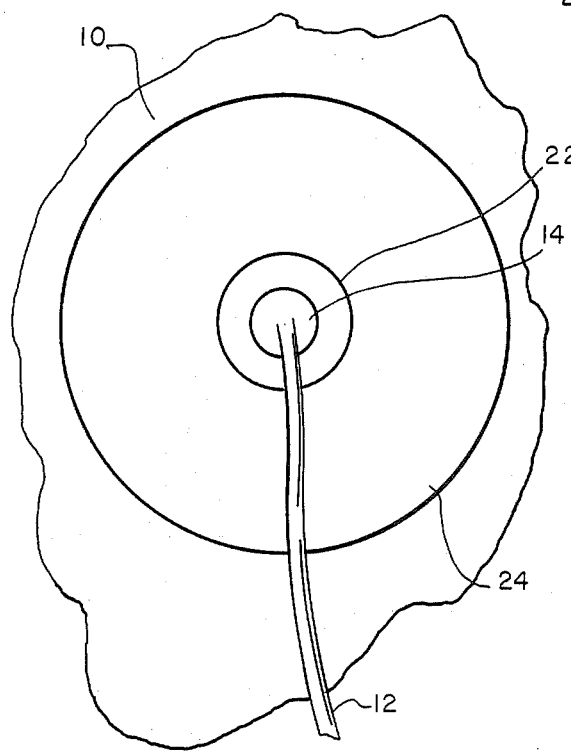
FIG. 5 shows a designated point with a tubular cylinder and electrode in plan view.
Figure 6:
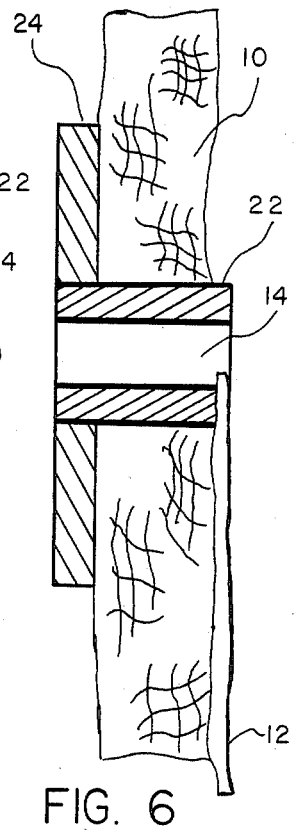
FIG. 6 shows the designated joint of FIG. 5 in sectional view.

Referring to FIGS. 5 and 6 of the accompanying drawings, in another embodiment an electrode 24 placed on the inside of the garment 10 might be connected to the conductor 12 either directly or through a conducting tubular cylinder 22 as shown. In this embodiment the electrode is selected for use by switching in the external device 18 rather than by application of conducting fluid alone.

Referring to FIGS. 7 and 8 of the accompanying drawings, in another embodiment the garment 10 has a pocket 26 of conductive material attached at the designated point 14 on the outer surface. The conductor 12 passes between the outer surface of the garment 10 and the pocket 26. Application of a conducting fluid into this pocket 26 results in soaking the garment 10 at the designated point 14 and in making contact between the conductor 12 and the wearer's skin. The pocket 26 aids in holding the conducting fluid. Application of the conducting fluid thus results in activating or selecting a designated point 14 for use, thus eliminating the need for external switching as in the previous embodiment.

Referring now to FIG. 9 of the accompanying drawings, in another embodiment the garment 10 has an electrode 38 on the inside of the garment. The conductor 12 crosses the designated point 14 on the surface in order to maintain insulation, between the conductor 12 and the wearer's skin. The area of the electrode 38 at the designated point 14 is covered by a piece of fluid-proof material 30 such as plastic sheet or coating in order to protect the outer garments from staining by the conducting fluid. The cover 30 is penetrated by an orifice 40 which has an orifice cover 42 which may be closed when desired such as after applying the conducting fluid. The electrode 38 may have a covering of non-conductive cloth 34 which is permeable to the conducting fluid. Applying conducting fluid through the orifice 40 connects the conducter 12 to the electrode 38 and through the permeable cover 34 to the wearer's skin.

Referring now to FIG. 10 of the accompanying drawings, the garment 10 is shown with the electrode 38 on the outside of the garment. The conductor 12 can cross the designated point either under or above the electrode 38. A fluid-proof cover 30 can be placed over the electrode. The orifice 40 with orifice cover 42 penetrates the fluid proof cover 30. When conducting fluid is applied through the orifice 40 the electrode 38 is connected to the conductor 12 and the wearer's skin at the designated point.

Figure 11:
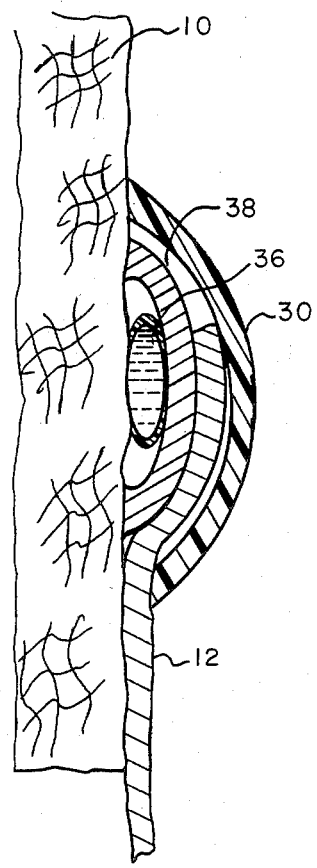
FIG. 11 shows a capsule of conducting fluid at the designated point in sectional view.

Referring now to FIG. 11 of the accompanying drawings, in another embodiment a capsule of conducting fluid 36 is shown assembled with the electrode 38. The capsule can be under or over the electrode 38 might be on the inside of the garment 10. The capsule 36 might similarly be assemblied on the inside of the garment. A fluid-proof cover 30 can be used with this embodiment without the need for an orifice or the orifice can be included to provide means for renewing the fluid. The capsule can be used to activate the electrode by breaking the capsule under finger pressure or pricking it with a needle or other tool.

Figure 12:
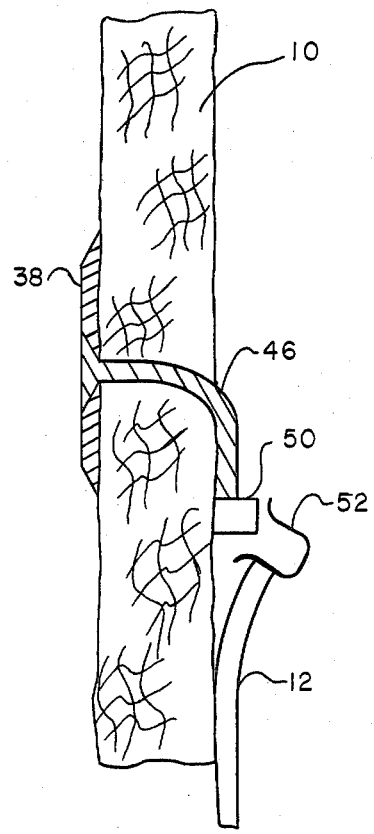
FIG. 12 shows in section view an embodiment using a selector terminal.

Referring now to FIG. 12 of the accompanying drawings, in another embodiment an electrode 38 is placed inside or outside the garment and connected by means of a short conductor 46 to a selector terminal 50. The use of the electrode can be selected by connecting the connector 52 to the selector terminal 50 and through the conductor 12 to the external electronics.

The conductors 12, electrodes 24 and 38 and pockets 26 may be metal or conductive cloth as HI-MEG. For example, in one embodiment, the HI-MEG is slit into 9/16 inch raw-edge strips. It is inserted into a folding attachment which, in conjunction for example with a 112 class sewing machine, automatically folds material into itself and feeds material on top of attire. This process forms a conductor 12 about 3/16 of an inch wide. Conductive fluid selecting pockets 26 of material are used in conjunction with the conductor 12 and are sized and placed according to need (i.e. T.E.N.S., E.M.S., F.E.S., EKG, EEG, EMG, etc.). Each stimulation and monitoring site pocket 26 utilizes conductive material cut to the desired size and shape for example, (1/32 inch in circumference to 2×6 inches). These cut conductive pockets 26 are then affixed to the conductor 12 at anatomically designated points 14 (e.g., T.E.N.S.: accupuncture points, trigger points and dermatones; E.M.S., F. E. S: motor points; EKG: standard chest and extremity points; EMG: EMG-points; EEG:EEG-points).

When the garment 10 is engineered for individual site monitoring or stimulation each designated point 14 has its own conductor 12 as in FIG. 1. A garment designed for stimulation is engineered with multiple designated points 14 on each conductor 12 as in FIG. 2 to allow multiple point active stimulation, or as in FIG. 1 in the alternative, the polarity for stimulation will generally be one half of garment 10 one pole and the opposite half the other pole. Entire garment 10 can be divided so that two or more pulse geneaurator can be set up, one for the top half and one for the bottom half of the garment. The base material of the garment can be of any suitable non electrical conducting material and constructed in the usual manner.

Each pocket 26 has for example a 1/64 inch to ½ inch application orifice 28, in each 3/2 inch segment, which allows for each application of a conductive fluid to the garment 10 subsequently penetrating to the skin without the need for pressure to push fluid through each pocket 26. This application orifice 28 also prevents the conductive fluid from having to be applied to the outer surface of the pocket 26 which may cause leakage onto outer attire. The garment 10 might be worn under a cast in order to employ EMS T.E.N.S., EMG OR EKG. In this case orifices connected via tubing can be cast in or placed through the cast in order to apply conductive fluid. A long term conductive liquid may be placed inside a pocket to be activated just prior to casting. The application tip of the conductive fluid dispenser is specially engineered to disperse an equal amount of conducting fluid through a small opening or openings allowing equal dispensing of the conducting fluid to the garment 10 subsequently penetrating to the wearer's skin. The pocket 26 with application orifice 28 can be combined with the tubular cylinder 22 and/or electrode 24 if desired. The application orifice provides for non-visual incertation of electrolyte.

The conductive paths can also be external to the garment. Hook-and-loop type cloth can be used to attach cloth to cloth without stitching. Such cloth is distributed by VELCRO USA, Inc. The disclosures of U.S. Pat. Nos. 2,717,437, 3,009,235, 3,417,440, 3,417,528, 3,461,513, and 3,708,382 are incorporated by reference. Such hook-and-loop cloth can be purchased as conductive cloth. Conductive hook-and-loop cloth can be used to connect designated points having pockets 26 made of conductive hook-and-loop cloth thereby eliminating the need for at least part, if not all, of the conductors sewed or glued into the garment. The connector to the external electrical apparatus can be terminated in a terminal of hook-and-loop cloth to facilitate interconnection in this embodiment.

Electrical conducting paths of conducting cloth sewed, glued, welded or attached by any other means into a garment can also be used for other functions besides monitoring the body or stimulating the body. In a space suit strips of conducting cloth can be connected to instruments, controls, air conditioning, lights and other electrical functions in place of wire. Such strips of cloth are more flexible than wires and less subject to breakage.

The non-conductive cloth of the garment might be nylon, Dacron ® polyester, cotton or rayon cellulose acetate or nonwovens or combinations of the foregoing. A nylon Lycra ® of 1 oz. to 20 ozs. weight would be suitable. The garment must be porous.

The conductive paths might be stitched on the surface of the garment glued, stapled or attached by equivalent method. The conductive path might also be knitted into the cloth, using a Jacquard Knitter, for example.

The hole in the pocket 26 might be fitted with a grommet to aid in applying the electrolyte. The grommet might be exchanged for a standard snap fastener with a hole 0.03 to 0.1 inch placed through the center. The snap could thus serve as an electrolyte conduit doubling as a snap for optional direct connection of wires. Examples of similar technology which could be used in combination with the pocket 26 are shown in U.S. Pat. No. 4,121,575 and 4,202,344, the disclosures of which are incorporated by reference. The tubular cylinder 22 is not limited to a circular cross section but may be elliptical or other in cross section.

The conductive fluid might range from most tap water, which contains suffiecient electrolyte to be workable for some stipulation applications, to standard electrode gel. An example of such standard electrode gel would be Signagel ® Electrode Gel distributed by Parker Laboratories of Orange, New Jersey, having the following properties. Physical description: viscous, clear, aqueous, saline gel, light green tint. Chemical composition: polymer, humectants, surface active agent, FDA certified color, sodium chloride, preservatives and dionized-ultra-violet-water. Preservative: propyl paraben and methyl paraben. Viscosity: 180,000 to 260,000 cps (Brookfield viscometer Model RVT, T-C spindle, 2.5 RPM). PH range: 5.4 to 6.4 (Beckman pH Meter Model 3500). Conductivity: 5,000 to 45,000 micro-ohms. Sterility: bacteriostatic. Safety: skin and eye irritation scored by Draize method; concluded that gel was not irritating to rabbit eyes and skin. Shelf life: indefinite. Precautions: no special handling required. Brussels nomenclature: other pharmaceuticals, 30.05 subitem No. 541.9(9). Other electrolytes might be as in U.S. Pat. Nos. 2,872,926, 3,528,408 and 3,607,788, the disclosures of which are incorporated by reference.

The tubular cylinder 22 might be made of plastic or rubber in the non-conductive embodiment. In the conductive embodiment the tubular cylinder 22 and the electrode 24 might be made of metal or silicone rubber.

In FIG. 13, there is taught an electrode arrangement that depicts another configuration for the assembly. For instance, at the site or point an electrode is positioned. The electrode may have a disc-like configuration or it may have any other desirable configuration from oblong to a free form configuration. The electrode 38 proper is constructed of the Hi-Meg material mentioned in the above. It is covered with an insulating material 30 of an area dimension and configuration to cover the electrode 38. The assembly is attached along a peripheral portion thereof as by sewing to the garment 10 at said site to form an electrolytic gel receiving pocket defined by the electrode 38 and an appropriate portion of the garment. From FIG. 15 the sewn seam 51 can be seen. The electrode is sewn onto the garment 10 over the conductor 12 as illustrated.

Orifice 40 in this embodiment is a short plastic tubular element terminating in a small annular flange 40A which constitutes the means to which the electrode is secured as by sewing. FIG. 15 depicts a seam 52 for this purpose.

FIGS. 13 and 14 depict the cover 42A for the orifice 40 as being a separate friction fitted plug. The plug has a stopper portion 42A which extends internally of the orifice and has an enlarged portion 42A having a slightly larger diameter than the orifice 40 to provide a finger nail grip for manual removal prior to loading the pocket with electrolytic gel and for re-insertion thereafter.

In a further modification as demonstrated by FIG. 16, the electrode 38 has sandwiched between its exposed surface and the garment a piece of cloth 53 of similar or like material. Cloth 53 may also be 100% polyester. It has a similar configuration as the electrode means and is sewn to the garment 10 when the electrode means is sewn or suitably affixed thereto. As the orifice communicates internally beyond the electrode 38 but not through the cloth 53 the pocket thereby formed is defined by the electrode 38 and the said cloth 53. The latter has the property of wicking the electrolytic gel supplied to the pocket in the direction of the garment 10 and therethrough thereof. The cloth 53 gives a controlling effect whereby the migration of the electrolytic gel beyond the area defined by the electrode means is inhibited.

Figure 17:
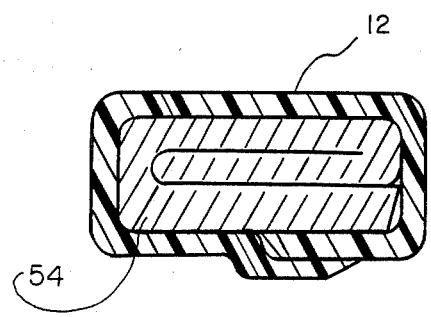
FIG. 17 is a cross-sectional view of another embodiment of the conducting pathway.

The conductor pathways 12, and 12A as depicted by FIG. 17 is constructed of the aforementioned Hi-Meg material 54. In this embodiment it is constructed from elongated pieces which are folded over longitudinally to provide a narrower dimension. The thusly folded conductive material 54 is then encased in a non-conducting web material which is illustrated in FIG. 17 as being a non-conducting cloth. The thusly encased conducting pathway is secured as by sewing to the outer surface of the garment 10 for the purposes as heretofore stated. In the sites where electrodes are to be positioned the Hi-Meg material 54 may be exposed or reliance may be had on the electrolytic gel to achieve an adequate electric pathway between the wrapped Hi-Meg material 54 and the electrode 38.

It is pointed out that in the assembly of the electrode means to the garment the conducting pathways 12 may be first sewn in place on the outer surface of the garment 10 and then the electrode means may be suitably sewn in place over the appropriate portion of the pathways 12. As the electrode means are fitted to the garment subsequently to the fixing of the electric pathways, it is contemplated that within the purview of the invention a garment may be prepared with appropriate electric pathways but no electrode means until a professional practitioner determines and selects the appropriate sites 14 at which time the electrode means are positioned and suitably affixed to the garment as by sewing, for instance.

This invention is not limited to the embodiments heretofore described, to which variations and improvements may be made, consisting of mechanically and electrically equivalent modifications to component parts, without leaving the scope of the present patent, the characteristics of which are summarized in the following claims.

What is claimed is:

1. A garment apparatus for delivering or receiving electric impulses comprising:
   a garment made of non-electrically conducting web material having small interstices;
   at least one thin electrode element, said electrode element having an orifice therethrough and being secured to said garment externally thereof in a manner to overlie a portion of said garment;
   at least one electrically conducting elongate pathway, one end of said pathway adapted and constructed to be in selective electrical contact with electrical impulse supplying means or electrical sensing means, the said pathway having a portion that is in electrical contact with said electrode element when said garment apparatus is in use;
   the electrode element being secured to said garment permitting a space to be defined between said electrode element and that portion of the garment over which said electrode element overlies said garment;
   the said orifice of said electrode element adapted and constructed to permit the introduction of electrolytic fluid-like material therethrough where by said fluid-like material may be introduced into said space;
   whereby said space is provided with a wicking means for drawing said fluid-like material to the garment so that said fluid-like material will penetrate said small interstices of said garment wherein the skin of a patient is wetted by said fluid-like material when said garment is worn to thereby complete the electrical connection between said electrode element and the skin of the patient.

2. The garment apparatus of claim 1 wherein the electrode element and the wicking means have disk-like configurations.

3. The garment apparatus of claim 2 wherein the electrode element and the wicking means are flexible.

4. The garment apparatus of claim 3 wherein the electrode element is secured along its peripheral portion to the garment.

5. The garment apparatus of claim 4 wherein the wicking means is cloth and is secured along its peripheral portion to the garment.

6. The garment apparatus of claim 5 wherein the cloth is formed of polyester.

7. The garment apparatus of claim 6 wherein the electrode element and the wicking means are secured along their peripheral portions to the garment by being sewn thereto.

8. The garment apparatus of claim 1 wherein the garment is constructed of woven material.

9. The garment apparatus of claim 1 wherein the garment is constructed of non-woven material.

10. An electrode assembly for delivering or receiving electric impulses to or from the skin of a living body comprising:
- a non-electrical conducting web material having small interstices;
- a thin flexible electrode element, said electrode element having an orifice therethrough and being secured peripherally to said web material in confronting relationship permitting a space to be defined between said electrode element and said web material;
- said orifice of said electrode element adapted and constructed to permit the introduction of electrolytic fluid-like material therethrough whereby said fluid-like material may be introduced into said space;
- whereby said space is provided with a wicking means for drawing said fluid-like material to the web material so that said fluid-like material will penetrate said small interstices of said web material wherein the skin of a patient is wetted by said fluid-like material when said electrode assembly is used to thereby complete the electrical connection between said electrode element and the skin of the patient.

11. The electrode assembly of claim 10 wherein the wicking means is cloth and is secured along its peripheral portion to the garment.

12. The electrode assembly of claim 11 wherein the cloth is formed of polyester.

13. The electrode assembly of claim 11 wherein the electrode element and the wicking means having disk-like configurations.

14. The electrode assembly of claim 13 wherein the electrode element is flexible and secured along its peripheral portion to the web material.

15. The electrode assembly of claim 14 wherein the electrode element and the wicking means are secured along their peripheral portions to the web material by being sewn thereto.

16. The electrode assembly of claim 10 wherein the web material is woven.

17. The electrode assembly of claim 10 wherein the web material is non-woven.

* * * * *